United States Patent [19]

Kawashima et al.

[11] Patent Number: 5,180,522
[45] Date of Patent: Jan. 19, 1993

[54] COLLOID SOLUTION FOR PREPARING SUSPENSION HAVING BOTH FLUIDITY AND SUSPENSIBILITY

[75] Inventors: Yoshiaki Kawashima, 185, Shimotsuchii, Gifu-shi, Gifu-ken; Taro Iwamoto, Nagoya; Kikuo Tejima, Toyoake, all of Japan

[73] Assignees: Yoshiaki Kawashima, Gifu; Showa Yakuhin Kako Co., Ltd., Tokyo, both of Japan

[21] Appl. No.: 165,013

[22] Filed: Mar. 4, 1988

[30] Foreign Application Priority Data

Mar. 6, 1987 [JP] Japan .................................. 62-52571

[51] Int. Cl.$^5$ ............................................. B01J 13/02
[52] U.S. Cl. ................................ 252/311; 252/315.3; 106/197.2; 106/208; 424/488
[58] Field of Search ............................. 252/311, 315.3; 424/488; 514/944, 965; 106/208, 197.2

[56] References Cited

U.S. PATENT DOCUMENTS 4,708,834 11/1987 Cohen et al. .................. 514/944 X
4,726,966 2/1988 Kawashima et al. ........... 424/462 X

OTHER PUBLICATIONS

Condensed Chemical Dictionary 9th Ed. Revised Hawley, Van Nostrand Reinhold, 1979.
Program and Abstracts of the 15th International Symposium on Controlled Release of Bioactive Materials, Basel, Aug. 15-19, 1988, Published by the Controlled Release Society, Inc.
Nakagaki, M.: "The Electrokinetic Potential of Some Sulfamines.", Yakugaku Zasshi 85 (10) 894-898 (1965); Physicochemical Studies on the Suspension Syrup. 3., Seminar Report No. SIB-R08, by Iwamoto, Taro.
Martin, Eric W.: Husa's Pharmaceutical Dispensing, Sixth Edition, Machk Publishing Company, Easton, Pa., pp. 89-91, 1966.
Ogata, Hiroyasu et al: Journal of Pharmacobio-Dynamics, "Development and Evaluation of a New Peroral Test Agent GA-Test for Assessment of Gastric Acidity", vol. 7 No. 9, Sep. 1984., Pharmaceutical Society of Japan, pp. 656-664.

*Primary Examiner*—Marianne M. Cintins
*Assistant Examiner*—Catherine Scalzo
*Attorney, Agent, or Firm*—Oblon, Spivak, McClelland, Maier & Neustadt

[57] ABSTRACT

A colloid solution for preparing a suspension, containing one or more components selected from Group A and one or more components selected from Group B as dispersoids, and water as a dispersant medium, the colloid solution being at a pH such that suspensoid particles added thereto are positively charged; wherein Group A consists of xylitol, D-sorbitol, D-mannitol, lactose, saccharose, cyclodextrin, maltose, D-fructose, D-glucose and galactose; and Group B consists of sodium carboxymethylcellulose, sodium alginate, sodium polyacrylate and gum arabic.

6 Claims, 1 Drawing Sheet

5,180,522

COLLOID SOLUTION FOR PREPARING SUSPENSION HAVING BOTH FLUIDITY AND SUSPENSIBILITY

BACKGROUND OF THE INVENTION

The present invention relates to a colloid solution for preparing a medicinal suspension with a very low viscosity, and also relates to a suspension including a colloid solution as a suspension medium.

Oral liquid medicines have greatly improved in taste and smell so as to be easily administered. Thus, there is even fear that children, on their own, might overindulge in the liquid medicine. An example of these liquid medicines is suspended medicinal syrup. This syrup has some advantages, for example, a slightly soluble medicine can be prescribed as a liquid.

The prior art medicinal suspensions, however, have a problem of balance between fluidity and suspensibility, which are properties contrary to each other. If the priority is attached to suspensibility, the poor fluidity of the suspension causes its handling to be difficult in measure or administer. On the other hand, if the importance is given to fluidity, insoluble or slightly soluble particles in the suspension are sedimented as a pasty cake. Namely, the suspensibility deteriorates to prevent the required amounts for administration from being measured accurately.

DESCRIPTION OF THE INVENTION

Accordingly, an objective of the invention is to provide a colloid solution for preparing a suspension having both sufficient fluidity and suspensibility.

A further objective of the invention is to provide a medicinal suspension including a colloid solution as a suspension medium.

Still a further objective of the invention is to provide a medicinal suspension in which suspended particles obtain the masking ability and release controllability for the control of medicinal concentration in the blood.

The above and other related objects are realized by a colloid solution including one or more components selected from group A and one or more components selected from group B as dispersoid and water as a dispersion medium at a specified hydrogen ion concentration. The group A consists of a monosaccharide such as xylitol, D-sorbitol and D-mannitol, an oligosaccharide such as lactose, saccharose, cyclodextrin, maltose, D-fructose, D-glucose and galactose and a polyhydric alcohol such as ethylene glycol, glycerin and propylene glycol. The group B consists of sodium carboxymethylcellulose (CMC-Na), sodium alginate, sodium polyacrylate and gum arabic.

The components selected from the group A and the group B are dissolved in water respectively and then are mixed together to prepare a colloid solution. When CMC-Na is used as the B group component, for example, its aqueous solution is prepared to be 0.5 to 1 weight % in concentration. If, furthermore, D-sorbitol is selected from the group A, 50 to 400 g of D-sorbitol is admixed with 500 cc of the above CMC-Na solution. In this case, the hydrogen ion exponent (hereinafter referred to as pH) of the colloid solution is controlled to be equal to or less than 4.5, but is preferable at below 2.4 when the CMC-Na concentration is 1 weight % and is preferable at below 2.0 when it is 0.5 weight %. When pH is over a specific value, the colloid solution of this invention can not be prepared. The specific pH value should adequately vary according to the components selected in both the group A and the group B. Components of more than two may be selected from each group.

The B group component of the colloid solution is considered to gel or to have a net structure. When fine particles for medicinal purposes are added to the above colloid solution, this specific structure works to capture the fine particles in the matrices thereof so as to make a suspension. Namely, the structure prevents the particles from sedimenting but allows the suspension to be stable despite the low viscosity. If the particles, i.e., suspensoid, is charged positively, the suspension further becomes more stable. The above specific structure is attained by a low pH and dehydration effects of the A group component. The low pH weakens the affinity of the B group component and water, and the dehydration effects of the A group component weakens the interaction between water and the B group component. As a result, the interaction in B group component itself strengthens to form the specific structure. For example, CMC-Na may be the B group component and a monosaccharide, an oligosaccharide or a polyhydric alcohol may be the A group component in the colloid solution at below pH 4.0.

EXAMPLES

Figure 1:
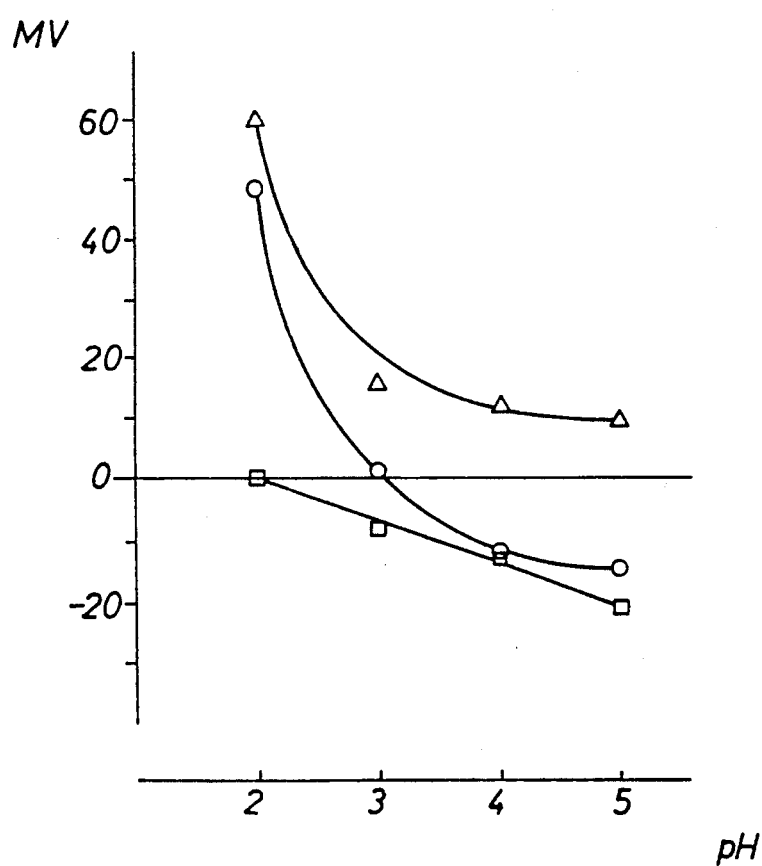
FIG. 1 shows zeta potential in a second example.

Examples of this invention are described hereinafter. Since there may be many modifications, however, without departing from the scope of the invention, the examples below are not intended to limit the invention to the examples, but are intended to illustrate the invention more clearly.

EXAMPLE 1

Certain amounts of CMC-Na (as B group component) and D-sorbitol (as A group component) according to Table 1 are mixed together in water to prepare various colloid solutions. The colloid solutions are controlled by dilute hydrochloric acid to attain various pH values, and then three types of ibuprofen fine particles are suspended in each colloid solution. The stability of each suspension is measured and the results are shown in Table 1. Here, a value in the CMC Na column shows the weight % of CMC-Na aqueous solution. A value in the D-sor column shows the amount (g) of 70 weight % of D-sorbitol aqueous solution mixed with a certain amount of the above CMC-Na solution. The amount of the fine particles suspended is 270 mg/10 cc. The marks, O, Δ and X represent the followings.

O: high stability;
Even after half a year, sedimentation does not occur.
Δ: low stability;
After one month, sedimentation occurs slightly.
X: lability;
After three hours, sedimentation starts.
The particle numbers represent the followings.

| 6181: | average particle diameter 250 μm |
| 7143-1: | 350 μm |
| 7143-2: | 150 μm |

In the example 1, fluidity of the suspension is enough to handle the suspension easily.

TABLE 1

| No. | CMC-Na | D-Sor | Particle No. | pH 2.7 | 2.6 | 2.5 | 2.4 | 2.0 |
|---|---|---|---|---|---|---|---|---|
| 1 | 1% | 200 g/500 cc | 6181 |  | Δ | O | O | O |
|  |  |  | 7143-1 |  | X | O | O | O |
|  |  |  | 7143-2 |  | O | O | O | O |
| 2 | 0.7% | 200 g/500 cc | 6181 |  | X | X | O | O |
|  |  |  | 7143-1 |  | X | X | O | O |
|  |  |  | 7143-2 |  | X | X | O | O |
| 3 | 0.5% | 200 g/500 cc | 6181 |  | X | X | X | O |
|  |  |  | 7143-1 |  | X | X | X | O |
|  |  |  | 7143-2 |  | X | X | X | O |
| 4 | 1% | 200 g/500 cc | 6181 |  |  | Δ | O | O |
|  |  |  | 7143-1 |  |  | X | O | O |
|  |  |  | 7143-2 |  |  | O | O | O |
| 5 | 1% | 150 g/500 cc | 6181 |  |  | X | X | X |
|  |  |  | 7143-1 |  |  | X | X | X |
|  |  |  | 7143-2 |  |  | X | X | X |
| 6 | 1% | 100 g/500 cc | 6181 |  |  | X | X | X |
|  |  |  | 7143-1 |  |  | X | X | X |
|  |  |  | 7143-2 |  |  | X | X | X |
| 7 | 1% | 50 g/500 cc | 6181 |  |  | X | X | X |
|  |  |  | 7143-1 |  |  | X | X | X |
|  |  |  | 7143-2 |  |  | X | X | X |
| 8 | 1% | 200 g/500 cc | 6181 | X | Δ | O | O |  |
|  |  |  | 7143-1 | X | X | O | O |  |
|  |  |  | 7143-2 | X | O | O | O |  |

EXAMPLE 2

If the surface of the suspended particles is coated with macromolecules which remarkably generate positive charges thereon at a specified pH, stimulated is the adsorption of water soluble macromolecules, such as CMC-Na existing in the suspension, on the surface of the particles. The adsorption makes it possible to prepare a stable suspension with large sized particles (several hundred microns). The macromolecules used for coating is, for example, acrylic ones or quarternary ammonium-containing acrylic ones.

Z potential of ibuprofen particles coated with quarternary ammonium containing-acrylic macromolecules is measured at various pH values. The streaming Potential Analyzer ZP10B (Shimadzu) is used for measurement. Pressure is applied by nitrogen gas and distilled water at a certain pH is used as the moving phase. The samples measured are previously immersed in the moving phase sufficiently.

The results are shown in FIG. 1. The marks in the figure represent the followings:
O: ibuprofen coated with quarternary ammonium containing-acrylic polymer;
Δ: simple body of acrylic polymer containing quarternary ammonium; and
□: untreated ibuprofen crystal.

EXAMPLE 3

A stable suspension with release controllability can be prepared by varying the proportion of a coating substance with respect to a medicine suspended.

Experiment 1

Ibuprofen: quarternary ammonium containing-acrylic macromolecules = 1:5 to 1:3

Ibuprofen particles of 250 μm in average diameter are suspended to prepare a stable fast-release type suspension having masking ability.

Experiment 2

Ibuprofen: quarternary ammonium containing-acrylic macromolecules = 1:3 to 1:2

Ibuprofen particles of 400 μm in average diameter are suspended to prepare a stable slow-release type suspension having masking ability.

The particles in both the Experiments 1 and 2 are not at all sedimented even after half a year and the each suspension maintains its low viscosity and release controllability. The colloid solution used as a suspension medium is prepared as follows. 200 g of 70 weight % solution of D sorbitol is admixed with 500 cc of 0.5 weight % solution of CMC-Na, and pH of the solution is then controlled to 2.0. The viscosity of the suspension is 60 cps, that is, the suspension has sufficient fluidity. The result of the Experiment 1 and Experiment 2 is shown in Table 2 and Table 3 respectively. The measurement is performed according to the Paddle method specified in the Japanese Pharmacopoeia and using the No. 2 liquid.

TABLE 2

| Hour(s) | Elusion Rate (%) |
|---|---|
| 1 | 88.8 |
| 2 | 97.9 |
| 3 | 100.0 |

TABLE 3

| Hour(s) | Elusion Rate (%) |
|---|---|
| 1 | 35.2 |
| 4 | 69.4 |
| 8 | 90.3 |

EXAMPLE 4

1 weight part of Eudragid RS and 3 weight parts of mefenamic acid (or tranilast) are mixed in ethanol to prepare granules (75 to 500 μm) by a wet method. The granules are suspended in a colloid solution including 500 cc of 0.5 weight % solution of CMC-Na and 200 g of 70 weight % solution of D-sorbitol at pH at 2. Even after 6 month-standing, the granules are not sedimented but the suspension is very stable while maintaining the sufficient fluidity.

EXAMPLE 5

Certain amounts of 70 weight % D-sorbitol solution and glycerin (A group component) are added to various concentrations of 500 cc CMC-Na solutions (B group component) according to Table 4 to prepare colloid solutions. The colloid solutions are controlled by dilute hydrochloric acid to attain various pH values, and then ibuprofen particles (400 μm in average diameter) are suspended. After 6 months has elapsed, the stability of the suspensions are measured and the results are shown in Table 4. The marks in the table represent the same as Table 1. The suspensions of this example have also maintained the sufficient fluidity for 6 months.

The above results show that addition of glycerin as one of the A group components does not cause stability change.

TABLE 4

| No. | CMC-Na Solution | D-Sor Solution | glycerin | pH 5.0 | 4.5 | 4.0 | 3.5 | 3.0 |
|---|---|---|---|---|---|---|---|---|
| 1 | 0.5% | 200 g/500 cc | 100 g/500 cc | X | X | X | X | X |
| 2 | 0.5% | 200 g/500 cc | 100 g/500 cc | X | X | X | X | O |
| 3 | 0.8% | 200 g/ | 100 g/ | X | X | X | X | O |

TABLE 4-continued

| No. | Component CMC-Na Solution | Component D-Sor Solution | Component glycerin | pH 5.0 | pH 4.5 | pH 4.0 | pH 3.5 | pH 3.0 |
|---|---|---|---|---|---|---|---|---|
| 4 | 1.0% | 500 cc 200 g/ 500 cc | 500 cc 100 g/ 500 cc | X | X | X | X | ○ |

EXAMPLE 6

Propylene glycol, ethylene glycol or D-glucose is added as the A group component to 500 cc of CMC-Na solution to prepare various colloid solutions at various pH values. Ibuprofen particles are then suspended in the colloid solutions. The stability of the suspensions are measured after 6 months and the results are shown in Table 5. The marks in the table represent the same as Table 1. The suspensions of this example have also maintained the sufficient fluidity for 6 months. The results show that propylene glycol, ethylene glycol and D-glucose can be used instead of D-sorbitol.

TABLE 5

| No. | CMC-Na Solution | Group A Component | pH | Stability |
|---|---|---|---|---|
| 1 | 0.5% | propylene | 0.97 | ○ |
| 2 | | glycol | 1.99 | ○ |
| 3 | | 200 g/500 cc | 3.00 | X |
| 4 | 0.5% | ethylene | 1.00 | ○ |
| 5 | | glycol | 1.97 | ○ |
| 6 | | 200 g/500 cc | 2.96 | X |
| 7 | 0.5% | D-glucose | 1.02 | ○ |
| 8 | | 200 g/500 cc | 2.01 | ○ |
| 9 | | | 2.96 | X |

EXAMPLE 7

Sodium alginate is used instead of CMC-Na. 500 cc of sodium alginate solution is mixed with 70 weight % of D-sorbitol solution to prepare a colloid solution at various pH values. Ibuprofen particles are then suspended in the colloid solutions. The stability of the suspensions are measured after 6 months and the results are shown in Table 6. The marks in the table represent the same as Table 1. The suspensions of this example have also maintained the sufficient fluidity for 6 months. The results show that sodium alginate can be used instead of CMC-Na.

TABLE 6

| Sodium alginate Solution | D-solubitol Solution | pH 1 | pH 2 | pH 3 | pH 4 | pH 5 |
|---|---|---|---|---|---|---|
| 0.5% | 200 g/500 cc | ○ | ○ | ○ | X | X |

What is claimed is:

1. A colloid solution for preparing a suspension, comprising one or more components selected from Group A and one or more components selected from Group B as dispersoids, and water as a dispersant medium, the colloid solution being at a pH such that suspensoid particles added thereto are positively charged; wherein said Group A consists of xylitol, D-sorbitol, D-mannitol, lactose, saccharose, cyclodextrin, maltose, D-fructose, D-glucose and galactose; and said Group B consists of sodium carboxymethylcellulose, sodium alginate, sodium polyacrylate and gum arabic.

2. The colloid solution as claimed in claim 1, wherein the component from group B is sodium carboxymethylcellulose, the concentration thereof being 0.5 to 1.0 weight %.

3. The colloid solution as claimed in claim 2, wherein the component from group A is D-sorbitol, 50 to 400 g of D-sorbitol being mixed with 500 cc of said sodium carboxymethylcellulose solution.

4. The colloid solution as claimed in claim 3, wherein a hydrogen ion component of said colloid solution is equal to or less than 4.5.

5. The colloid solution as claimed in claim 4, wherein said pH of said colloid solution is less than 2.4.

6. The colloid solution as claimed in claim 5, wherein said pH of said colloid solution is less than 2.0.

* * * * *